United States Patent [19]

Hut

[11] Patent Number: 5,159,933

[45] Date of Patent: Nov. 3, 1992

[54] DEVICE FOR TAKING A SAMPLE OF SUBCUTANEOUS TISSUE CELLS FROM A BODY

[75] Inventor: Pieter K. H. Hut, Haren, Netherlands

[73] Assignee: Metrias, B.V., Netherlands

[21] Appl. No.: 455,392

[22] PCT Filed: Apr. 18, 1989

[86] PCT No.: PCT/NL89/00025

§ 371 Date: Jan. 6, 1990

§ 102(e) Date: Jan. 6, 1990

[87] PCT Pub. No.: WO89/10092

PCT Pub. Date: Nov. 2, 1989

[30] Foreign Application Priority Data

Apr. 18, 1989 [NL] Netherlands ............... 8801002

[51] Int. Cl.⁵ ............................................. A61B 10/00
[52] U.S. Cl. ......................................................... 128/753
[58] Field of Search ............ 128/753, 754, 760, 763, 128/765, 770; 606/170, 171

[56] References Cited

U.S. PATENT DOCUMENTS

| | | | |
|---|---|---|---|
| 4,641,663 | 2/1987 | Juhn | 128/765 |
| 4,655,226 | 4/1987 | Lee | 128/754 |
| 4,664,128 | 5/1987 | Lee | 128/753 |
| 4,817,631 | 4/1989 | Schrepp-Pesch et al. | 128/753 |

*Primary Examiner*—Max Hindenburg
*Attorney, Agent, or Firm*—Mark Zovko

[57] ABSTRACT

Device for taking a sample of subcutaneous tissue cells from a body, comprising a disposable injection syringe with a cylinder, a plunger slidably arranged in the cylinder and connected to an actuating shaft protruding outside the cylinder at one end, and a coupling element situated at the opposite end of the cylinder for the coupling thereto of an injection needle. The device further comprises pulling means for the exerting of a force on the plunger in the direction away from the coupling element. The pulling means comprise on one side energy transmitting biasing means coupled to the cylinder which exerts a tensile force on the plunger which after a movement of the plunger in the order of magnitude of 1 cm from an outer most position in contact with the end of the cylinder bearing the coupling element lies in the order of magnitude of 10 Newton times the diameter of the cylinder in cm².

9 Claims, 4 Drawing Sheets

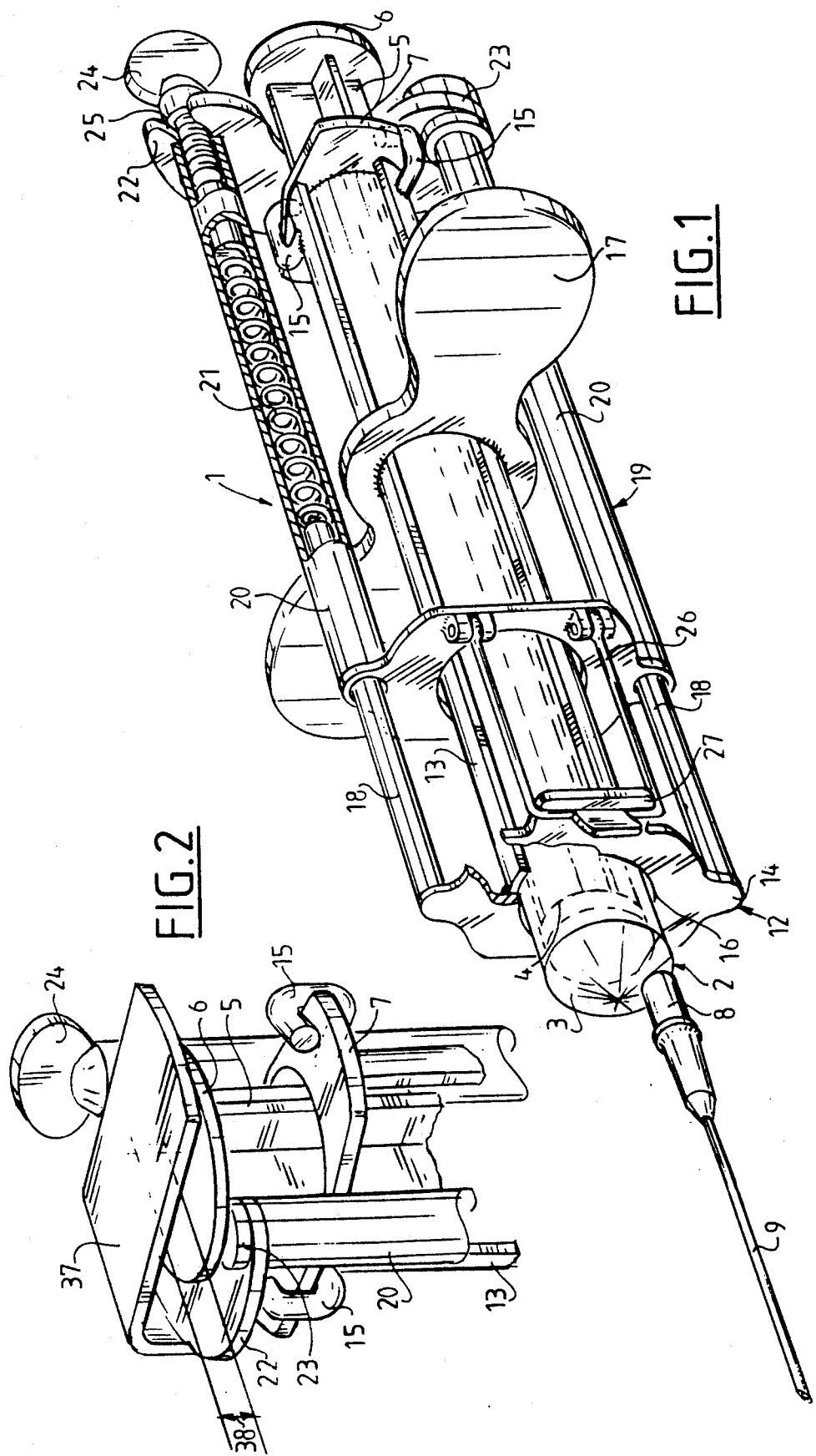

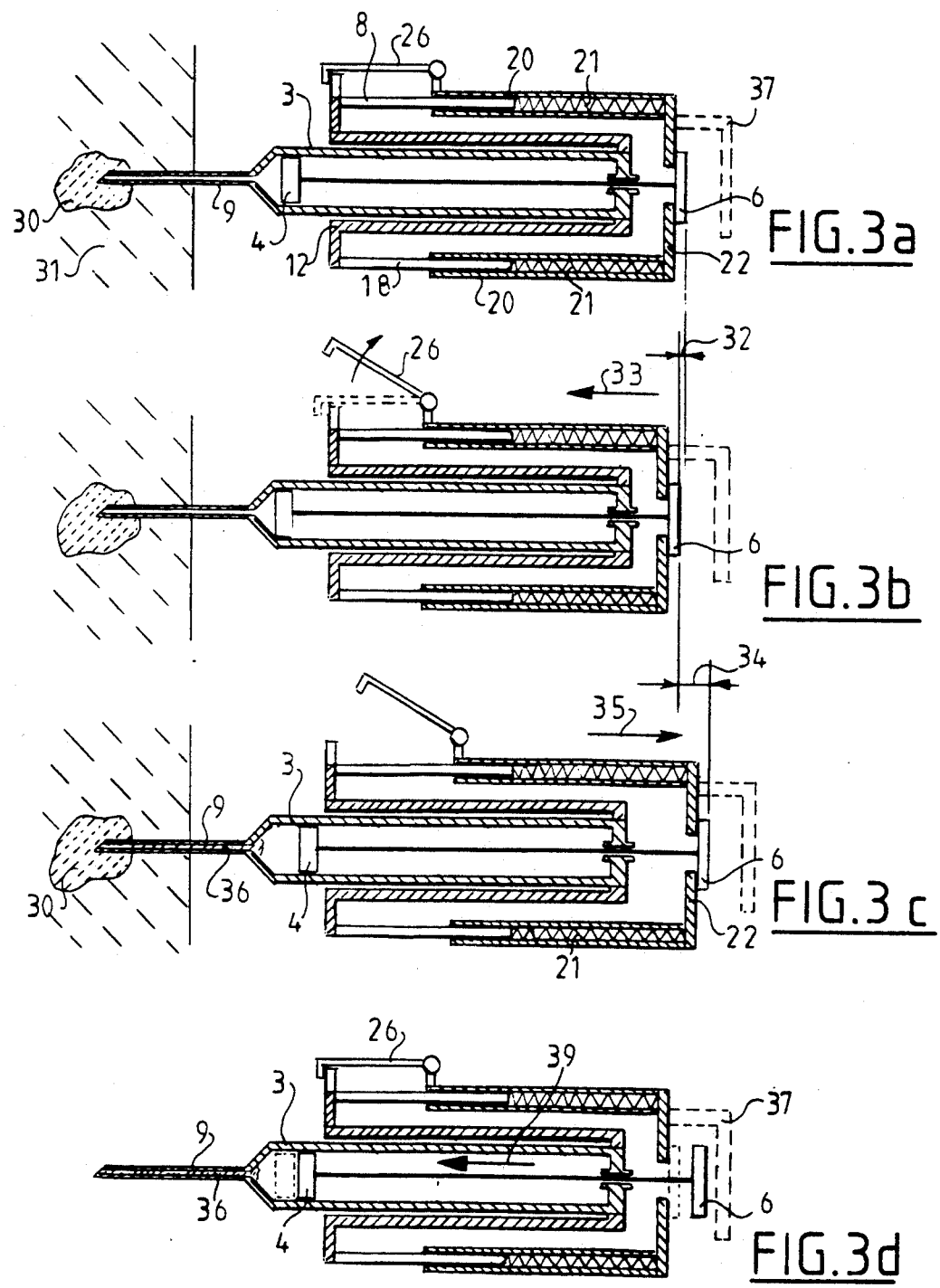

DEVICE FOR TAKING A SAMPLE OF SUBCUTANEOUS TISSUE CELLS FROM A BODY

BACKGROUND OF THE INVENTION

1. Field of the Invention

This invention relates generally to a device for taking a sample of tissue cells from a body and more particularly a syringe for taking a sample of subcutaneous tissue cells from a body.

2. Description of the Prior Art

Such a device is known from International patent application WO 88/01882. The pulling means for exerting a force on the plunger in the direction away from the coupling element are formed by a holder wherein a disposable injection syringe can be accomodated. A first holder part of this known holder comprises a hand grip with a support connected thereto at a distance by guiding rods for the second holder part into which the cylinder of a disposable injection syringe with the finger rest protruding transversely thereto can be clamped fixedly. The second holder part is provided with an opening in which can grip two fingers of a hand holding the hand grip. Using an injection syringe arranged in this holder a suction action can be applied instead of the usual injecting action. Such a suction action is for example applied in taking a sample of cell material, in particular for the purpose of cytological testing. This testing can be used for determining whether a tumour is benign or malignant. For the collection of the cell material the needle of the injection syringe is inserted into the tumour after which the plunger of the syringe is drawn out so that an underpressure is created in the syringe and an amount of cell material is sucked into the needle. It is usual in collecting the cell material to move the needle back and forth a number of times so that sufficient cell material is released. The quantity of the collected material is otherwise usually very limited and then substantially to the capacity of the needle itself.

In order to avoid the material being drawn into the cylinder forcibly by through-flowing air and becoming so spread out there that it is no longer usable for the test, the underpressure must first be neutralized again by moving back the plunger before removing the needle.

The known holder is awkward in use. On withdrawal of the plunger a cramped hand position arises which either makes difficult a sensitive and controlled guidance of the injection syringe needle or makes it impossible. Moreover, the distance from the hand to the area where the needle is inserted is great so that precise and sensitive handling is also made difficult as a result. Further, the assembly of holder with disposable injection syringe is bulky and in the position of use is in fact held in the same position as a pistol, which has an at least disturbing effect on the patient being treated.

SUMMARY OF THE INVENTION

The aim of the invention is to provide a holder of the present sort which obviates these drawbacks. This aim is achieved according to the invention with the steps mentioned subsequently herein. After insertion of the injection needle the biasing means provide the generating of the suction. With only a limited displacement of the plunger from the outermost position an equilibrium is created between the force exerted on the plunger by the underpressure generated and the force exerted by the biasing means. Because of this the device can be held in a more relaxed manner. This enables sensitive control and use of the device.

Underlying the invention to a significant extent is the insight that the plunger of the injection syringe does not need to be withdrawn to the maximum, as is usual, but only for a very limited distance in order to generate suction suitable for the removal of the cell material. Because the distance through which the plunger is withdrawn is relatively small the device can also take a small form and this contributes to sensitive handling of the device and moreover the more compact form thereof is experienced by the patient as less threatening.

As a result of the present invention it becomes unnecessary during the insertion of the injection needle to exert a force countering the biasing means so that the insertion of the needle can be performed with the very desirable sensitivity.

Achieved in a very favourable manner with the present invention is that during use of the device it is ensured that when the plunger is made to move back into the cylinder of the injection syringe at the end of the operation the plunger is prevented from being pressed downward with positive force which could result in the possibility that the collected cell material is pressed out of the injection needle again. When the finger rest is pressed in the plunger moves back until the underpressure under the plunger is removed. Should the finger rest be pressed in further the plunger is not pressed further downward by the free stroke in the transmission.

The device is preferably embodied in its entirety as a disposable device for once-only use.

A favourable alternative embodiment of the device is disclosed. By making use of standard disposable injection syringes usage costs can be lowered.

In a preferred embodiment of the invention the portion of the plunger adjoining the injection needle protrudes out of the passage opening and therefore remains in sight during use. The operation can for example be adapted as a result should it be apparent that fluid is being drawn up.

The finger rest arranged according to the present invention is situated relatively close to the end of the injection syringe bearing the injection needle, which contributes to a good and sensitive control of the assembly.

When using the present invention the holder with injection syringe can be held in position in the hand in a natural manner which again contributes to its user friendly character.

In the present invention the transport with the free stroke can still be achieved in a simple and reliable manner.

It should be noted that an injection syringe provided with biasing means in the form of a spring is known from American patent specification U.S. Pat. No. 4,641,663. This known injection syringe is not suitable for taking a sample of subcutaneous tissue cells but is intended for the drawing up of a quantity of liquid. Only a limited amount of spring force is needed to draw up liquid and moreover the plunger can be moved through a relatively great distance by the spring.

The invention will be further elucidated in the following description of a number of embodiments.

BRIEF DESCRIPTION OF THE FIGURES

FIG. 1 shows in partly sectional perspective view a device according to the invention in the embodiment of a holder having accommodated therein a standard disposable injection syringe.

FIG. 2 shows a portion of another embodiment of the device in FIG. 1.

FIGS. 3a–d show schematically the action of the device from FIGS. 1 and 2.

DETAILED DESCRIPTION OF THE PREFERRED EMBODIMENT

Figure 4:
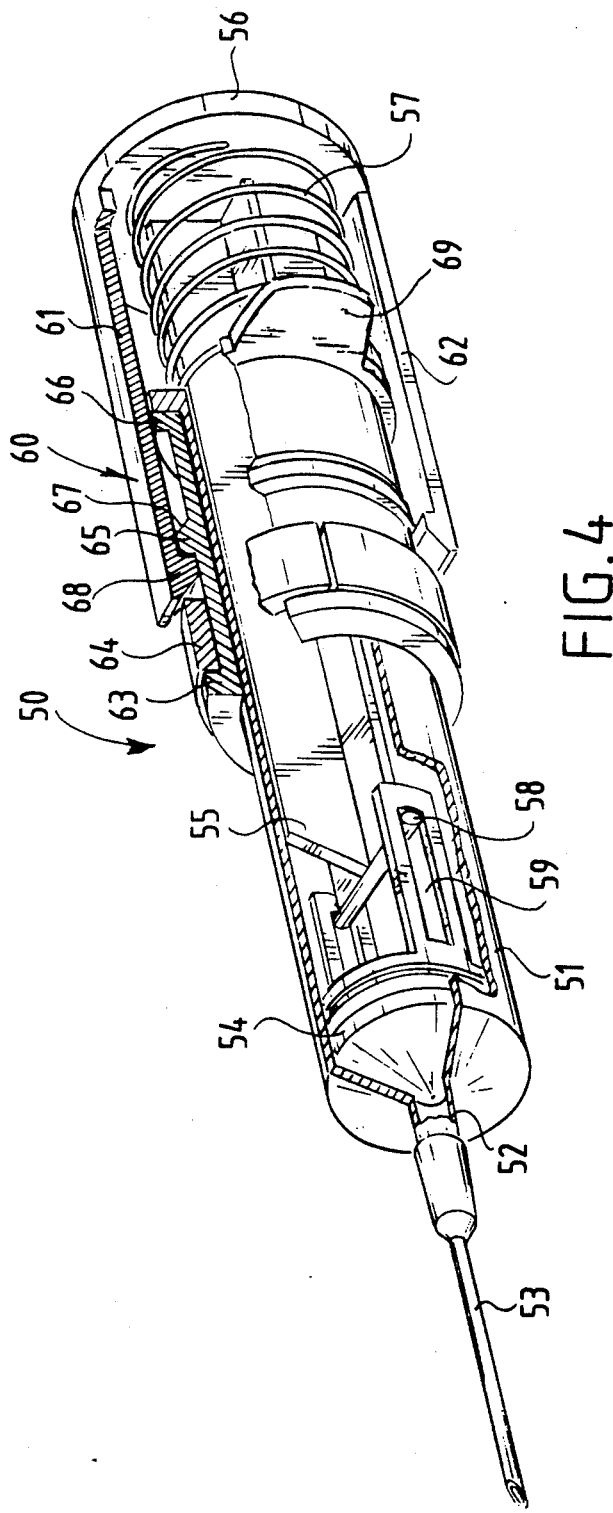
FIG. 4 shows in partially broken away perspective view a device according to the invention in the embodiment of a disposable device for once-only use.

In the device according to the invention shown in FIG. 1 a disposable injection syringe 2 is accommodated in the holder 1. The disposable injection syringe 2 consists in the generally known way of a cylinder 3, a plunger 4 arranged slidably in the cylinder 3 and connected with an actuating shaft 5 protruding outside the cylinder 3 at one end and an injection needle 9 coupled thereto by a coupling element 8 at the end of the cylinder 3 situated opposite the protruding actuating shaft end. The actuating shaft 5 bears at its protruding end a thumb rest 6 while finger rests 7 are formed at the end lying close to the cylinder 3.

The holder 1 comprises a first holder part 12 wherein the cylinder 3 of the disposable injection syringe can be fixed. This first holder part 12 comprises a sleeve-like body 13 connected fixedly to an end plate 14. The end plate 14 is provided with a passage opening 16 through which the end of the cylinder 3 bearing the needle 9 can protrude. At the opposite end the sleeve-like member 13 carries gripping means 15 which can clamp the finger rests 7 on the cylinder 3. These gripping means 15 are embodied such that these act as a bayonet closure whereby the disposable syringe 2 can be fixed very simply in the holder.

Connected to the end plate 14 are two guiding pins 18 which extend parallel to the longitudinal direction of the holder. A second holder part 19 comprises sleeves 20 with which this second holder part 19 is slidably mounted onto the pins 18 of the first holder part 12. The bottom guide sleeve 20 of the second holder part 19 in FIG. 1 carries a closing plate 22 hinging at 23. The closing plate 22 is provided on the opposite side with a slot 25 which can grip around the shank of a wing screw 24. The closing plate 22 can be fixed in position with the wing screw 24 which grips into the uppermost sleeve 20. The closing plate 22 protrudes beneath the thumb rest 6 of the actuating shaft 5 and can thus grip this thumb rest 6.

Coil springs 21 are arranged in the sleeves 20. These coil springs 21 form biasing means which can force the gripping means 15, 22 of the first and second holder part 12, 19 away from one another. In other words the springs 21 force the second holder part 19 to the right as seen in FIG. 1 relative to the first holder part 12. When an injection syringe 2 is arranged in the holder 1 the plunger 4 is then loaded thereby in the sliding out direction.

The holder 1 with the disposable injection syringe 2 arranged therein is held with one hand in the manner usual for an injection syringe, whereby the thumb rests on the thumb rest 6 and the index and middle finger respectively on either side of the sleeve-like member 13 on the finger rest 17 arranged on this member 13.

As shown in FIG. 1 the finger rest 17 is arranged at a distance from the gripping means 15 on the side away from the closing plate 22. Thus created during use is a suitable distance between the finger rest 17 and the thumb rest 6 which is favourable for controlled handling of the holder with syringe. The hand in which the holder is held is moreover located relatively close to the injection needle 9 so that during use sensitive and accurate control of the assembly is possible.

As shown the second holder part 19 bears a ratchet bracket 26 which can grip onto a ratchet projection 27 on the end plate 14 of the first holder part 12. The ratchet bracket 26 is of a length such that the holder parts 12, 19 can be blocked counter to the force of the springs 21 in the position whereby the gripping means 15, 22 are closest to each other, that is, in the position whereby in use the plunger 4 is entirely pushed into the cylinder 3.

It will be apparent that the disposable syringe 2 is arranged in the holder 1 as seen in FIG. 1 on the right-hand side thereof, whereby the closing plate 22 is swivelled away about the hinge 23. After the insertion of the cylinder 3 in the sleeve-like member 13 and turning thereof through a limited angle such that the finger rests 7 engage with the gripping means 15 the closing plate 22 is swivelled back to the position shown in FIG. 1 and secured using the screw 24. When the plunger is subsequently pushed completely into the cylinder 3 and the ratchet bracket 26 is brought into engagement with the ratchet projection the assembly is in the ready-for-use position.

In FIG. 3a the assembly is schematically shown in this read-for-use position. The use of the holder according to the invention is as follows.

In the ready-for-use position as described above the holder having therein a disposable injection syringe 2 is inserted with its needle 9 into tissue 31 in order to remove a quantity of cell material therefrom. The holder according to the invention is particularly but not exclusively intended for removal of a quantity of cell material from a tumour 30 in order that cytological testing can be carried out on that cell material.

As previously noted, the holder parts are temporarily blocked during the insertion of the injection needle 9 into the tumour 30 by the ratchet 26 counter to the force of the biasing means formed by the springs 21. The insertion can therefore be performed with great sensitivity since the forces arising during insertion are not masked by forces for the tensioning of the springs 21.

After insertion, as is shown in FIG. 3b, the thumb rest 6 is pushed in a short distance 32 in the direction of the arrow 33, as a result of which the ratchet 26 can be released. The ratchet 26 can be spring loaded so that it automatically springs loose. The ratchet can also be released by hand.

Subsequently, as shown in FIG. 3c, the force on the thumb rest 6 is reduced causing the springs 21 to displace the first holder part to the right. The closing plate 22 thereby grips under the thumb rest 6 and the plunger 4 is therefore also moved in the cylinder 3 to the right. The springs 21 are preferably dimensioned such that an equilibrium of forces results as soon as the plunger 4 is withdrawn a distance in the order of magnitude of 1 cm. For this purpose the springs are dimensioned such that after a displacement in the direction of the arrow 35 over a distance 35 in the order of magnitude of 1 cm they exert a force in the order of magnitude of 10 Newton times the diameter of the cylinder in $cm^2$.

In the position of FIG. 3c the injection needle 9 is now moved back and forth a small distance in the tumour 30 as a result of which an amount of cell material 36 is freed which is sucked up in the needle 9. Again, the hand holding the holder does not hereby need to exert force to maintain the underpressure so that these operations can also be executed with precision, control and sensitivity.

When sufficient cell material has been taken up the thumb rest 6 is pressed in again and the ratchet 26 is fixed in place. The underpressure in the cylinder is then hereby removed. The assembly can be subsequently withdrawn.

The cell material 36 collected in the needle 9 is further processed in the usual manner.

It is further noted that it is necessary for the underpressure to be removed before the needle is withdrawn in order to prevent cell material 36 being sucked into the cylinder forcibly through air being sucked in, which would make it practically impossible to remove this material from the disposable syringe for testing. This is otherwise per se known.

FIG. 2 shows a modification of the holder in FIG. 1. The corresponding parts are indicated with the same reference numerals so that further discussion thereof can be omitted. In relation to the embodiment in FIG. 1 a thumb rest 37 is arranged on the closing plate 22 protruding above the thumb rest 6 on the actuating shaft 5 and leaving free a space 38 of some millimetres above the thumb rest 6 on the actuating shaft 5. This thumb rest 37 is indicated schematically in FIGS. 3a-d with dashed lines. The thumb of the operating hand rests on this thumb rest 37 during use.

As discussed, at the end of the operation just before the withdrawal of the needle 9, the plunger 4 must move back into the cylinder 3 in order to remove the underpressure. This is performed by pushing back the second holder part counter to the force of the springs 21 in the direction of the arrow 39. As a result of the free stroke for the thumb rest 6 provided by the thumb rest 37 is now achieved that the plunger 4 moves back only under the influence of the underpressure and therefore does not move further once this underpressure is removed. The second holder part can still be moved slightly, which can be necessary for causing the ratchet 26 to grip. Since the plunger 4 only moves back under the influence of the underpressure and not because of a force applied to the thumb rest 6, partial pressing of the collected cell material 36 out of the needle 9 is prevented.

The device 50 as shown in FIG. 4 is of the type embodied as disposable device for once-only use. The device 50 comprises a cylinder 51, a plunger 54 slidably arranged in the cylinder 51 and connected in a manner further to be described to an actuating shaft 55 which protrudes outward from the cylinder 51 at the right-hand end as seen in FIG. 4 and which carries a thumb rest 56 at its end. At the opposite end the cylinder is provided in the usual manner with a coupling element 52 for coupling a needle 53 to the cylinder 51.

Arranged around the end of the actuating shaft 55 protruding out of the cylinder 51 is a spiral spring 57 which lies on one side against the cylinder 51 and on the other side against the underside of the thumb rest 56. The spring 57 can exert a force on the plunger 54 via the actuating shaft 55 in the direction away from the coupling element 52.

As shown the shaft 55 and therefore the finger rest 56 are coupled to the plunger 54 by a transmission with a free stroke. The shaft 55 bears on its end facing the plunger two cams 58 which grip into slots 59 which are formed in rearwrd facing protrusions connected to the plunger 54. In the manner described earlier this transmission with free stroke prevents the plunger 54 being unintentionally pushed too far in the direction of the needle 53 after the taking of the sample, which would result in the collected cell material 54 being pressed out of the needle 54 again.

The device 50 is also provided with ratchet means 60 for temporarily blocking the spring 57 counter to the force of the spring 57 in the most outermost position of the plunger 54. The ratchet means 60 are formed by two ratchet arms 61, 62 situated diametrically opposed to one another on the thumb rest 56 and a sleeve 63 provided with cams 65, 66 which is pushed over the cylinder 51. A freely slidable ring 64 is arranged on the sleeve 63. The ratchet arms 61, 62 bear on their end a ratchet 68 which can grip behind the first cam 65 and second cam 66 of the sleeve 63. The foremost cam 65 is provided on its rear side with a sloping surface 67 so that the ratchet 64 can easily slide over it during the movement, to be further described, from right to left as seen in FIG. 4.

The working of the device 50 is hereafter further elucidated with reference to the FIGS. 5a-e.

Figure 5A:
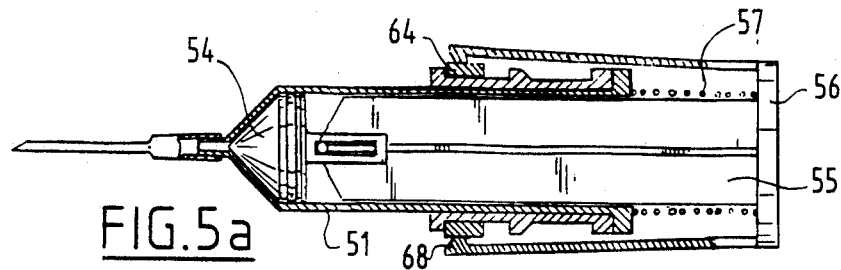
FIGS. 5a–e show schematically the action of the device according to FIG. 4.
Figure 5B:
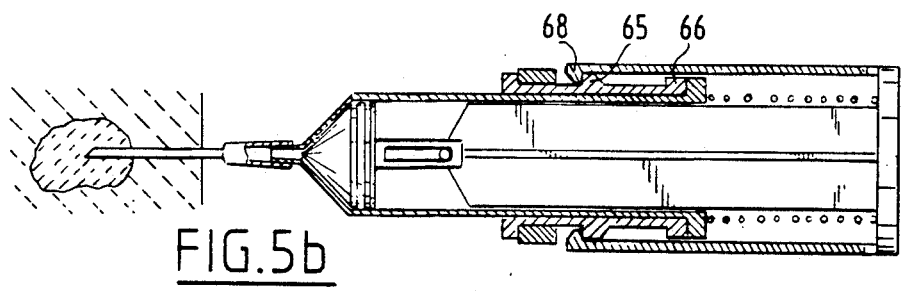
Figure 5C:
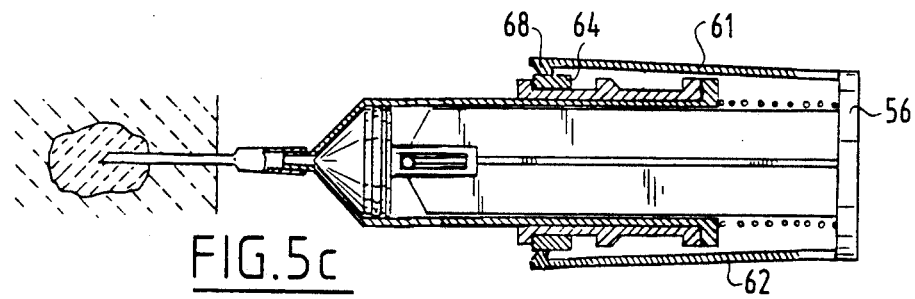
Figure 5D:
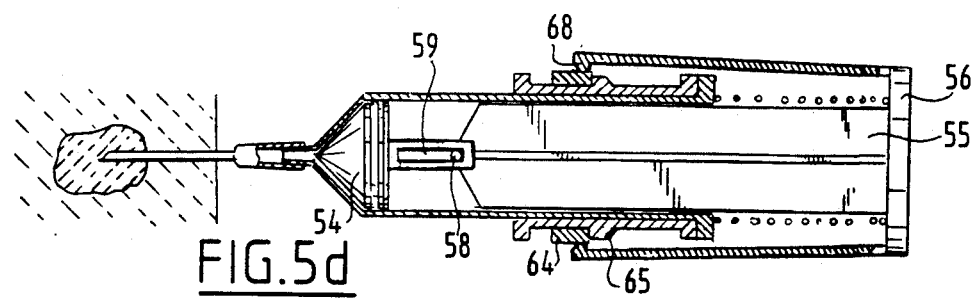

As preparation for the operation of taking a sample the plunger 54 in its outermost position is pressed into contact with the end of the cylinder 51 bearing the coupling element. This is shown in FIG. 5. The device 50 is held in the usual manner for an injection syringe, whereby the index finger and middle finger grip on either side of the cylinder behind the finger rests 69 and the thumb is held on the thumb rest 56. By pressing in the thumb rest 56 the cams 58 at the end of the actuating shaft 55 come up against the front end of the slot 59 so that the plunger 54 can be pressed completely forwards. The ratchets 68 can hereby slide onto the slide ring 64. The pressure on the thumb rest 56 is subsequently lessened as a result of which the spring 57 moves the actuating shaft to the right together with the component parts forming a whole with it. The slide ring 63 is hereby held in position so that it cannot co-slide. The ratchets 68 slide as a result off the ring 64 and are pressed inward through the resilient force of the ratchet arms 61, 62, thereby falling behind the first cam 65. This situation is shown in FIG. 5b. In this situation the needle is inserted. This can take place in the manner described earlier with sensitivity since no forces need to be further exerted on the device than are necessary for the insertion of the needle. Once the needle has been inserted in the required manner a force is once again applied to the thumb grip 56 with the thumb. The ratchets 68 of the ratchet arms 61, 62 consequently slide onto the slide ring 64 again. This situation is shown in FIG. 5c. By now once again relieving the pressure on the thumb grip 56 the actuating shaft 55 and the parts forming a whole therewith slide to the right as seen in FIG. 5. The ratchets 65 hereby take the slide ring 64 with them. The slide ring 64 thereby comes to a stop against the first cam 65. This position is shown in FIG. 5d. The cams 58 have hereby come into contact with the rear end of the slots 59. By now further reducing the pressure of the thumb the cams 68 slide from the ring and over the cam 65 so that the actuating shaft 55 can move further to the rear and can thereby pull the plunger 54 along with it.

Figure 5E:
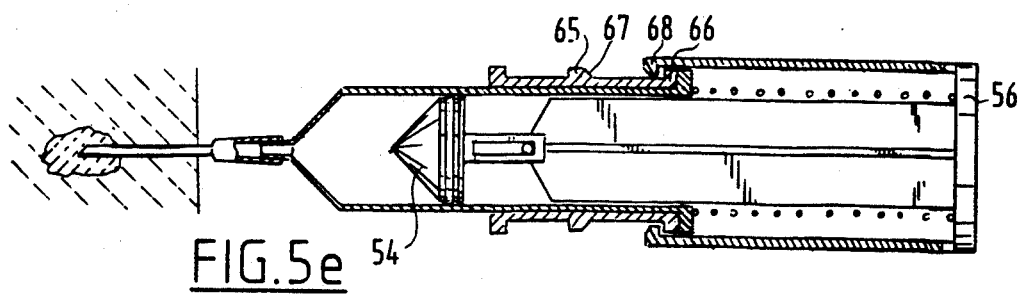

In this situation as shown in FIG. 5e the subcutaneous tissue cells can be collected in the manner described above.

When this operation has been completed the thumb rest 56 is again pressed to the left whereby the ends of the ratchets 68 move over the sloping edge 67 on the cam 65. With further movement to the left the ring 64 is pushed aside and the ratchets 68 can fall behind the cam 65. Thus reached again is the situation shown in FIG. 5b. The plunger 54 is only moved back under the influence of the underpressure created at the front side thereof so that in the situation thus achieved no more forces will act on the plunger 54, thereby preventing the collected cell material being pressed outward out of the needle or being sucked inward into the cylinder. With the ratchets 68 in engagement with the cam 65 the whole device can be withdrawn.

The second cam serves as end stop for the cams 68 so as to prevent an unintended manipulation causing the shaft with the plunger to come out of the cylinder under the influence of the action of the spring 57. When the spring 57 is dimensioned such that it is completely expanded before the shaft is withdrawn from the cylinder the cam 65 can be omitted. As shown the ratchet means comprise the separate sleeve 63 which can slide with a light grip fitting onto a cylinder of a standard disposable syringe. For the manufacture of the device according to the invention in this embodiment partial use can be made therefore of components which are already manufactured for standard disposable injection syringes. It is of course also possible to integrate a ratchet device with a cylinder.

The invention is not limited to the embodiments shown in the figures. It is important that during the puncturing the underpressure is developed by previously introduced energy. The biasing means can work in many other ways instead of with resilient force, such as for example with gas pressure. The preferably applied ratchet can be manually operated or automatically acting. Optionally the biasing means can take an adjustable form. In the case of use of springs, such as the springs 21, as biasing means, an adjustable end stop for these springs can be applied which results in it becoming possible to adjust the equilibrium underpressure occurring during use as required.

I claim:

1. Apparatus for taking a sample of subcutaneous tissue cells from a body comprising a disposable injection syringe with a cylinder; a plunger slidably arranged in said cylinder and connected to an actuating shaft protruding outside said cylinder at one end, and connected to a coupling element at the opposite end of said cylinder for the coupling thereto of an injection needle; and further pulling means for the exerting of a force on said plunger in the direction away from said coupling element, said pulling means including on one side energy transmitting biasing means coupled to said cylinder which exerts a tensile force on said plunger such that after a movement of said plunger in the order of magnitude of 1 cm from an outermost position in contact with the end of said cylinder bearing said coupling element, the tensile force on said plunger lies in the order of magnitude of 10 Newton times the diameter of said cylinder in $cm^2$.

2. The apparatus of claim 1 which includes ratcheting means for temporarily blocking said biasing means in an outermost position of the plunger counter to the force of said biasing means.

3. Apparatus as claimed in any of the above claims wherein the apparatus is embodied in its entirety as a disposable device for once-only use.

4. Apparatus as claimed in claims 1 or 2 which includes a holder for said disposable injection syringe, said holder including a first holder part with first gripping means for the cylinder, and a second holder part slidably connected to said first holder part with second gripping means for said actuating shaft and whereby said biasing means are connected to said first and second holder parts and force said first and second gripping means away from one another.

5. Apparatus as claimed in claim 4 wherein said first and second gripping means are arranged such that they can grip on first finger rests on respectively the cylinder and the activating shaft of said disposable injection syringe.

6. Apparatus as claimed in claim 4 or 5 wherein said first holder part includes a passage opening for said cylinder at the end of said cylinder away from said first gripping means.

7. Apparatus as claimed in any of the claims 4,5 or 6 which includes second finger rests at a distance from said first finger rests on the side away from said first finger rests for said actuating shaft.

8. The apparatus of claim 1 or 2 which includes a finger rest for actuating said plunger, said finger rest being coupled to said plunger by a transmission with a free stroke and that said biasing means are coupled directly with said finger rest.

9. The apparatus as claimed in any of the above claims in which said biasing means is a spring.

* * * * *